Figure 1:
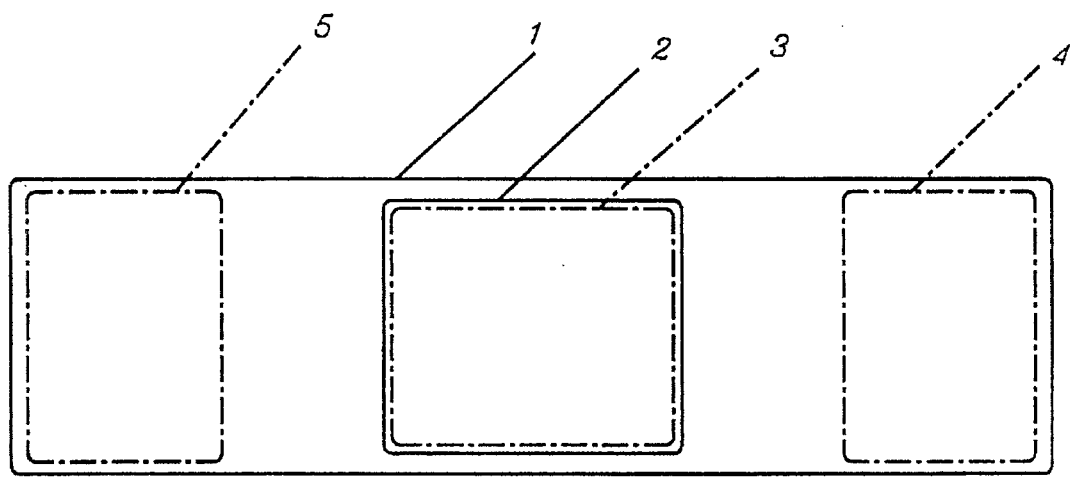

United States Patent [19]

Daneshvar

[11] Patent Number: 5,643,315
[45] Date of Patent: Jul. 1, 1997

[54] DEVICE FOR WOUND THERAPY AND PREVENTION OF BLEEDING

[76] Inventor: Yousef Daneshvar, 21459 Woodfarm, Northville, Mich. 48167

[21] Appl. No.: 310,349

[22] Filed: Sep. 22, 1994

[51] Int. Cl.$^6$ ............................................. A61B 17/12
[52] U.S. Cl. ............................................. 606/201; 606/202
[58] Field of Search .................... 128/118.1, 96.1, 128/638; 606/201, 202, 203, 204

[56] References Cited

U.S. PATENT DOCUMENTS

| | | | |
|---|---|---|---|
| 3,171,410 | 3/1965 | Towle, Jr. et al. | 602/53 |
| 4,224,945 | 9/1980 | Cohen | 606/201 |
| 4,436,089 | 3/1984 | Schmid | 602/53 |
| 4,583,546 | 4/1986 | Garde | 128/638 |
| 4,957,105 | 9/1990 | Kurth | 128/96.1 |
| 5,170,781 | 12/1992 | Loomis | 128/118.1 |

FOREIGN PATENT DOCUMENTS 9011744  10/1990  WIPO ............................... 606/202

*Primary Examiner*—Michael Powell Buiz
*Assistant Examiner*—Patrick W. Rasche

[57] ABSTRACT

This invention introduces a system which allows a low level of pressure to be applied to the wound site in order to prevent bleeding during a stable period. Some models of this unit also give the option of allowing the unit to be inflated in order to increase the pressure in the area and stop bleeding if it occurs later. Automatic ways of recognizing bleeding are also introduced that utilize a computerized means of recognition and/or application of a set of proper reactions after bleeding, and an automated pressure application as well. It is believed that this unit will help human beings significantly.

16 Claims, 9 Drawing Sheets

DEVICE FOR WOUND THERAPY AND PREVENTION OF BLEEDING

This application is related to the applicant's previous approved and/or pending applications, and the content of the following application is incorporated by reference as if it were fully disclosed herein. The applicant's previous applications are as follows D. Device, Pressure Bandages and Dressings, Device for Preventing Post-Catheterization Wound Bleeding, Device for Preventing Post-Catheterization Wound Bleeding, D. Device 4, Device for Applying Pressure to a Person'G groin, Daneshvar's Device 6 and Daneshvar's Device 7. The application for D. Device was applied on Nov 29, 1991, and the patent was granted on Nov 23, 1993 with U.S. Pat. No. 5,263,966

The application for the Pressure bandages, and dressings was applied on Oct 28, 1992 with Ser. #07/967,379, now U.S. Pat. No. 5,376,067.

The application for Device for Preventing Post-Catheterization Wound Bleeding was applied on Dec 14, 1992, with Ser. #07/989,825 now U.S. Pat. No. 5,423,852.

The application for Device for Preventing Post-Catheterization Wound Bleeding was applied on Apr. 5, 1993, with Ser. #08/042,560 U.S. Pat. No. 5,383,893.

The application for D. Device 4 was applied on Aug. 21, 1993, with Ser. #08/113,652 now abandoned.

The application for Device for Applying Pressure to a Person'G groin was applied on Dec. 14, 1993, with Ser. #08/165,835 now U.S. Pat. No. 5,514,155.

The application for Daneshvar's. Device 6 was applied on May 5, 1994, with Ser. #08/238,629 and is pending. The application for device to suppress bleeding at a wound site was applied on Aug. 8, 1994, with Ser. No. 08/287,307 and is pending. from Detroit.

THE BACKGROUND OF THIS INVENTION

Bleeding in a patient is worrisome, bothersome and at times a very dangerous problem. It can be due to injuries, surgeries or medical procedures. In any of these occurrences there is a need for prevention and treatment. For this reason this inventor as well as many others has introduced units to prevent bleeding in an acute stage. However, there is a need for a unit that can be used in a reasonably comfortable fashion in stages where there is no significant bleeding. However, the danger of bleeding still exists. This unit is to address such an issue and introduces units to be used in this stage, although they will be useful in many other conditions such as cuts and post surgical states. Furthermore some models of these units will allow pressure in the wound side to occur in a case of bleeding.

BRIEF EXPLANTION OF INVENTION

This invention introduces a unit that is primarily made from a pliable, non-stretchable support unit made from a fabric, a polymer such as vinyl or their combination that will be placed around the wound site. This unit will support a pressure-producing device such as a spring or lever system and particularly a balloon or an expandable unit in order to press the wound site to provide wound therapy and prevent bleeding. This application also introduces a method that allows the bleeding to be automatically detected by means such as electrical methods and computerized units which will be capable of reacting to bleeding as well to start a process and to increase the pressure in the wound site.

THE FIGURES

Please notice that the applicant respectfully requests to have the figures from his previous applications which are mentioned above to also be considered as part of the background of this invention. Also please notice that the new figures are started from 1 and the related numbers from 842A.

Brief mentioning of the figures:

FIG. 1. Shows a prototype unit with a clear balloon and a layer of adhesive on it.

Figure 2:
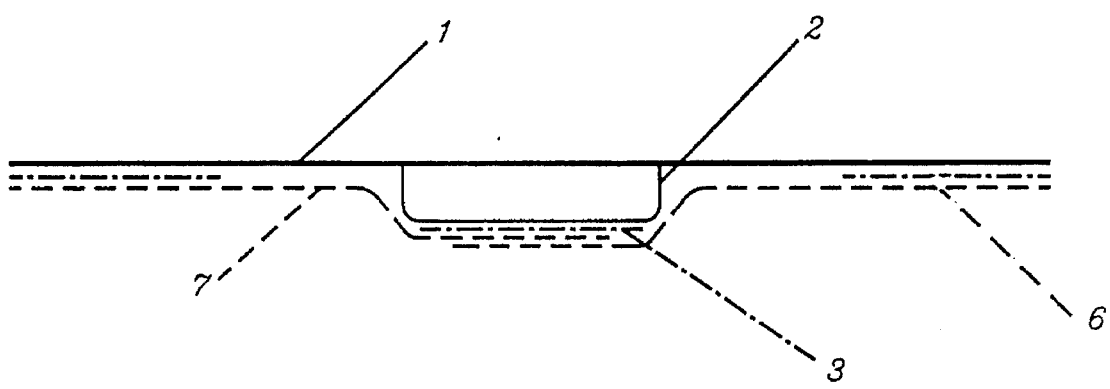

FIG. 2. Shows the cross-cut view of the unit shown at FIG. 1.

Figure 3:
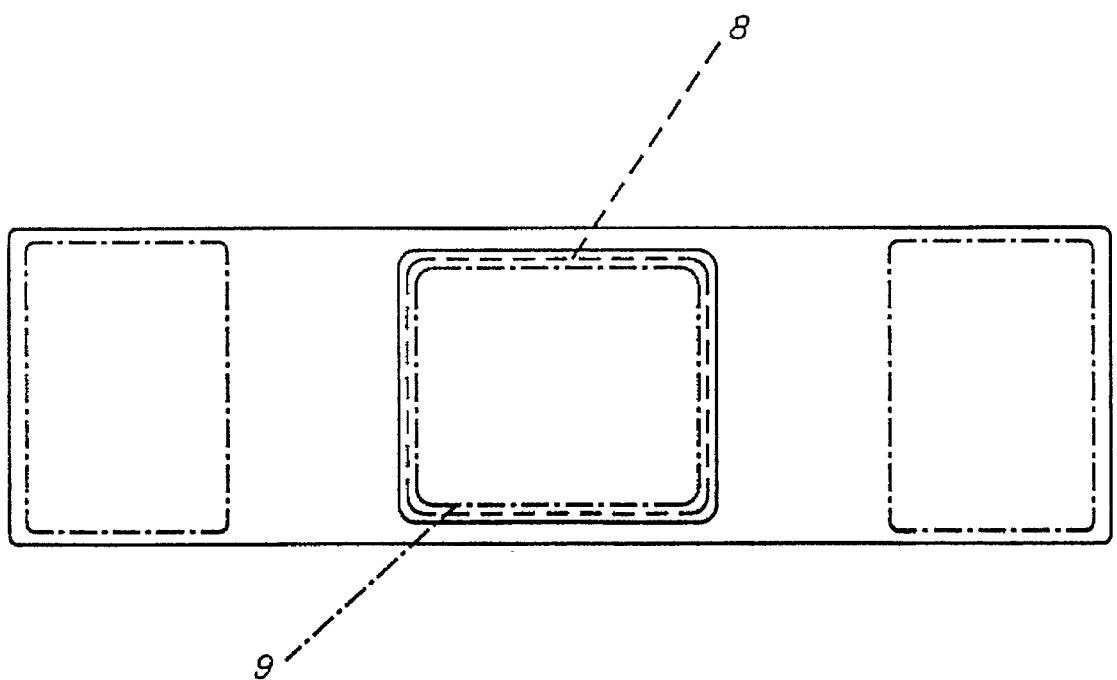

FIG. 3. Shows the from view of a unit with a piece of rigid, clear plastic and a layer of adhesive in its front.

Figure 4:
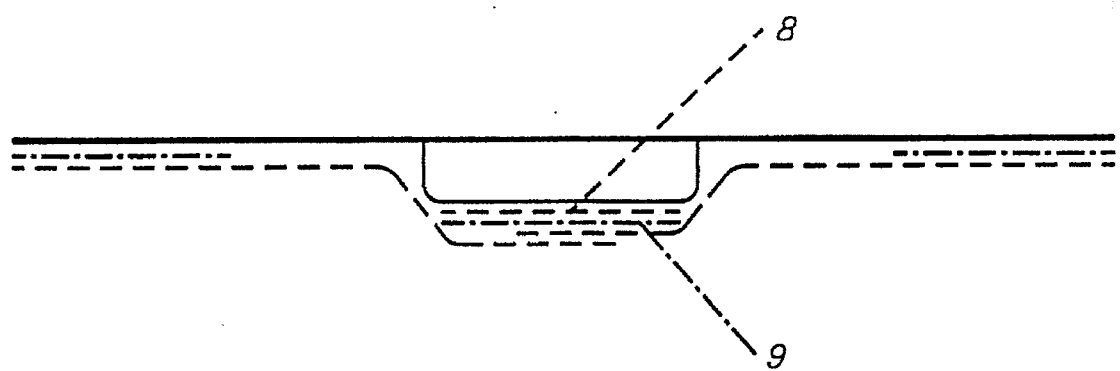

FIG. 4. Shows the cross-cut view of the unit shown in the previous figure of 3.

Figure 5:
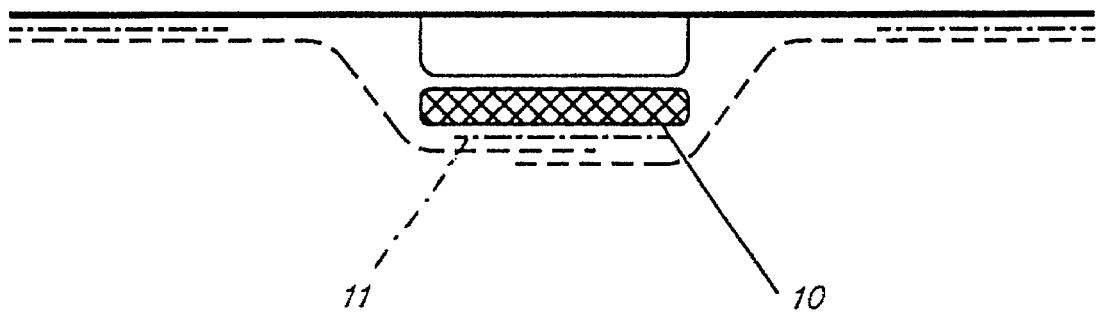

FIG. 5. Shows the cross-cut view of a unit with a pad of gauze in the front of the balloon.

Figure 6:
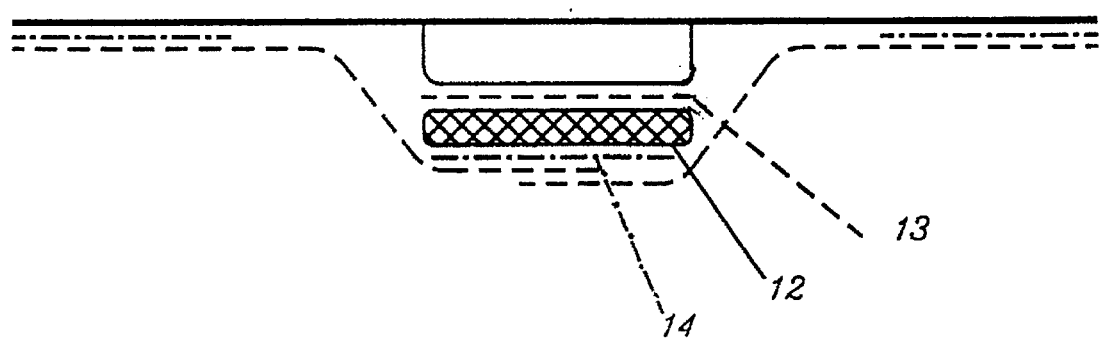

FIG. 6. Shows the cross-cut view of a unit which also has a piece of clear, rigid piece of plastic in its front.

Figure 7:
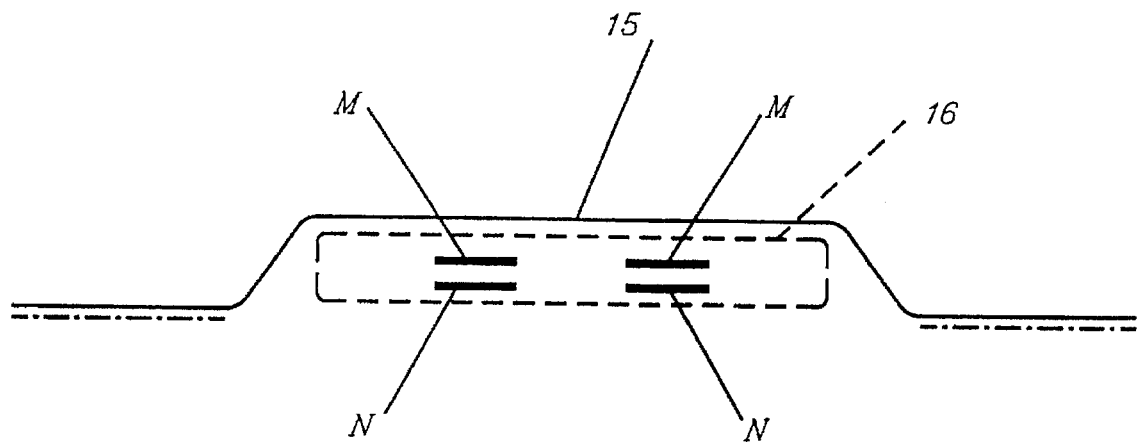

FIG. 7. Shows the cross-cut view of a unit with sensor leads inside the gauze pad.

Figure 8:
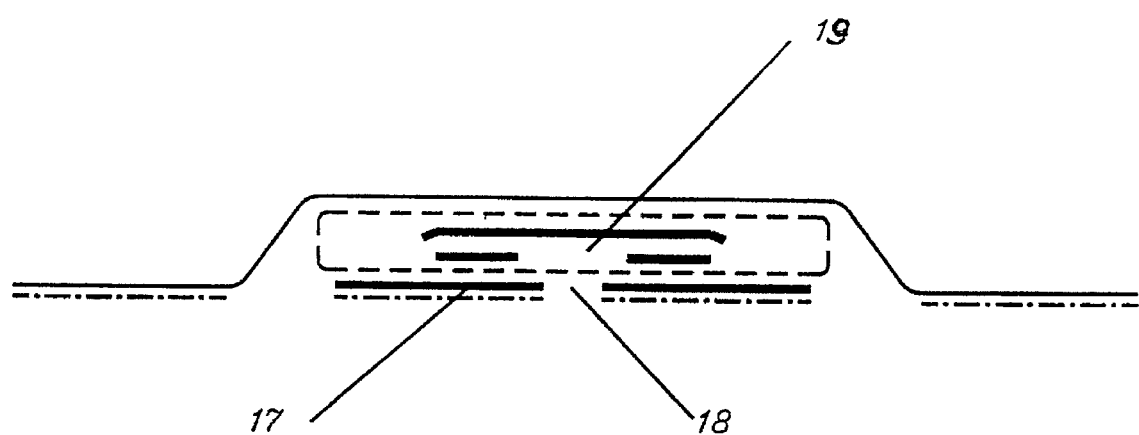

FIG. 8. Shows a different model with sensor units and a non-permeable layer in its front.

Figure 9:
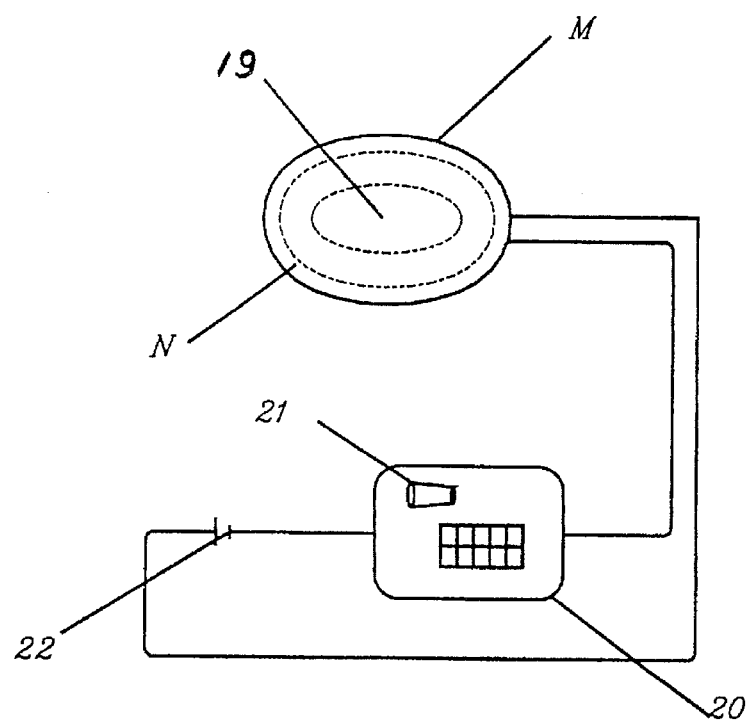

FIG. 9. Schematically shows how the bleeding detection system will be made and will function.

Figure 10:
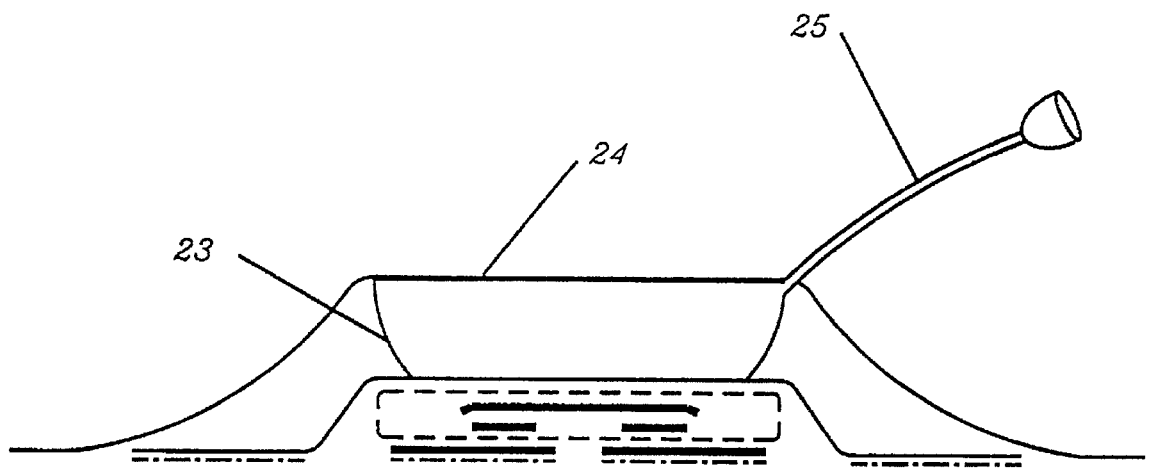

FIG. 10. Shows a unit with sensors inside a gauze pad and a balloon on its rear surface.

Figure 11:
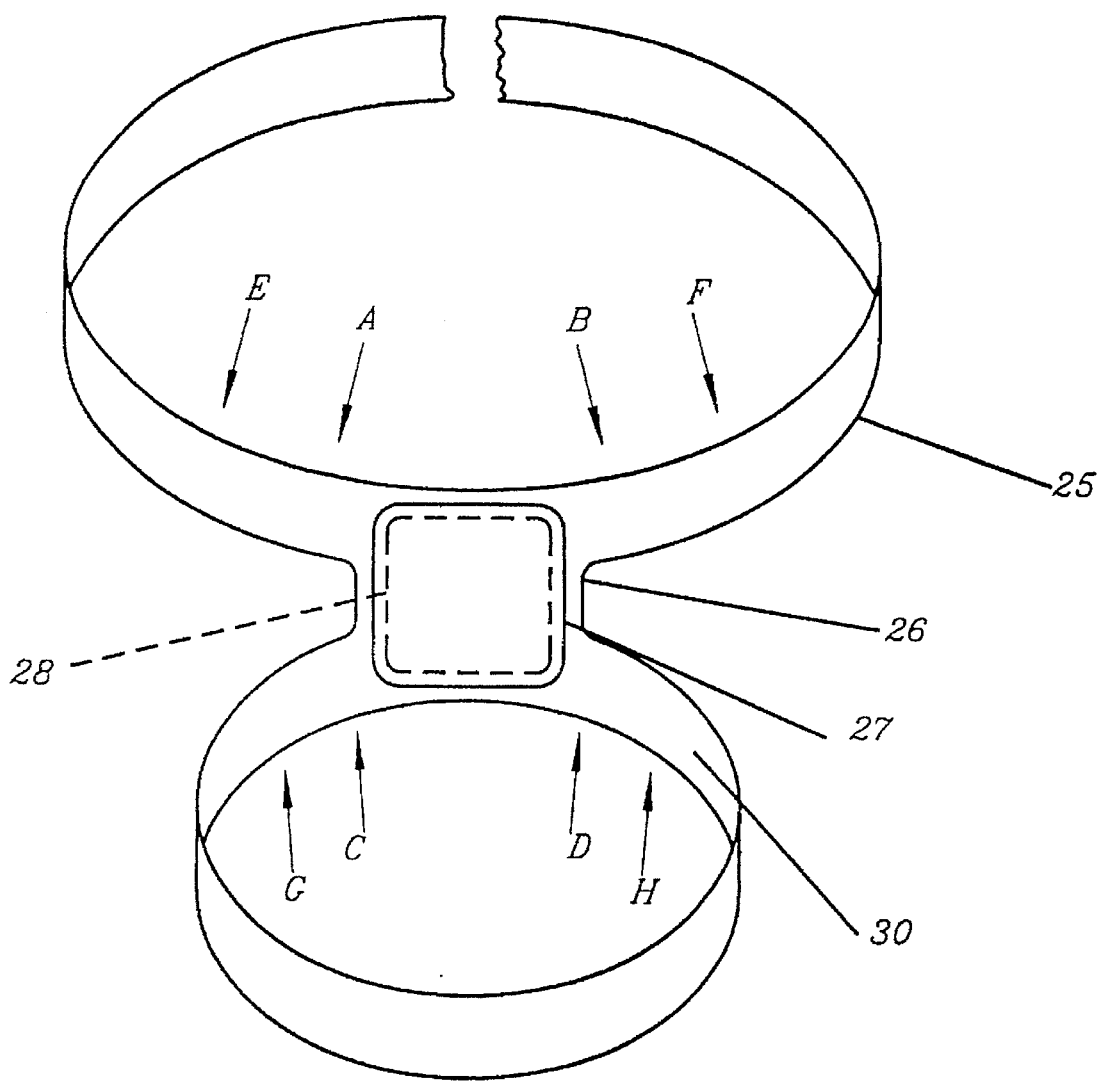

FIG. 11. Shows a unit to be used in the groin area.

Figure 12:
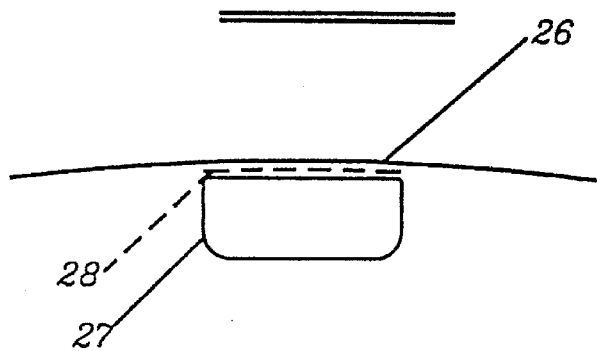

FIG. 12. Shows the cross-cut view of a unit similar to the one at FIG. 11 except it has a rigid piece at 28.

Figure 13:
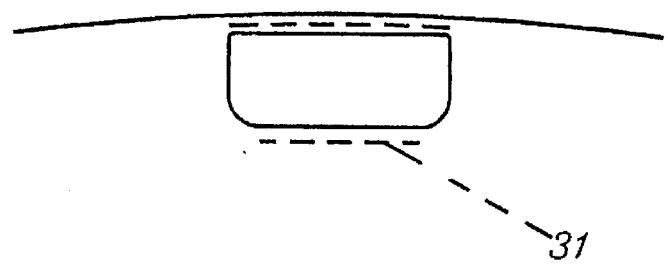

FIG. 13. Shows the cross-cut view of the unit similar to the one at FIG. 12 with a piece of rigid plastic in its front.

Figure 14:
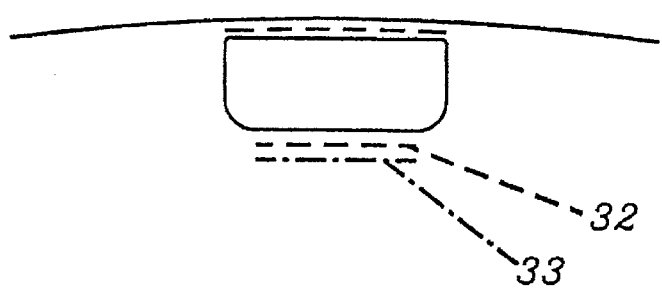

FIG. 14. Shows the cross-cut view of a unit similar to the one at FIG. 13 with a layer of adhesive film on its front.

Figure 15:
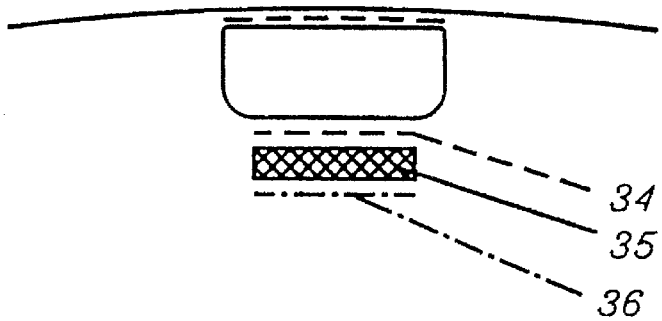

FIG. 15. Shows the cross-cut view of a unit similar to the one shown in the previous FIG. 14, with a layer of gauze pad in its front.

Figure 16:
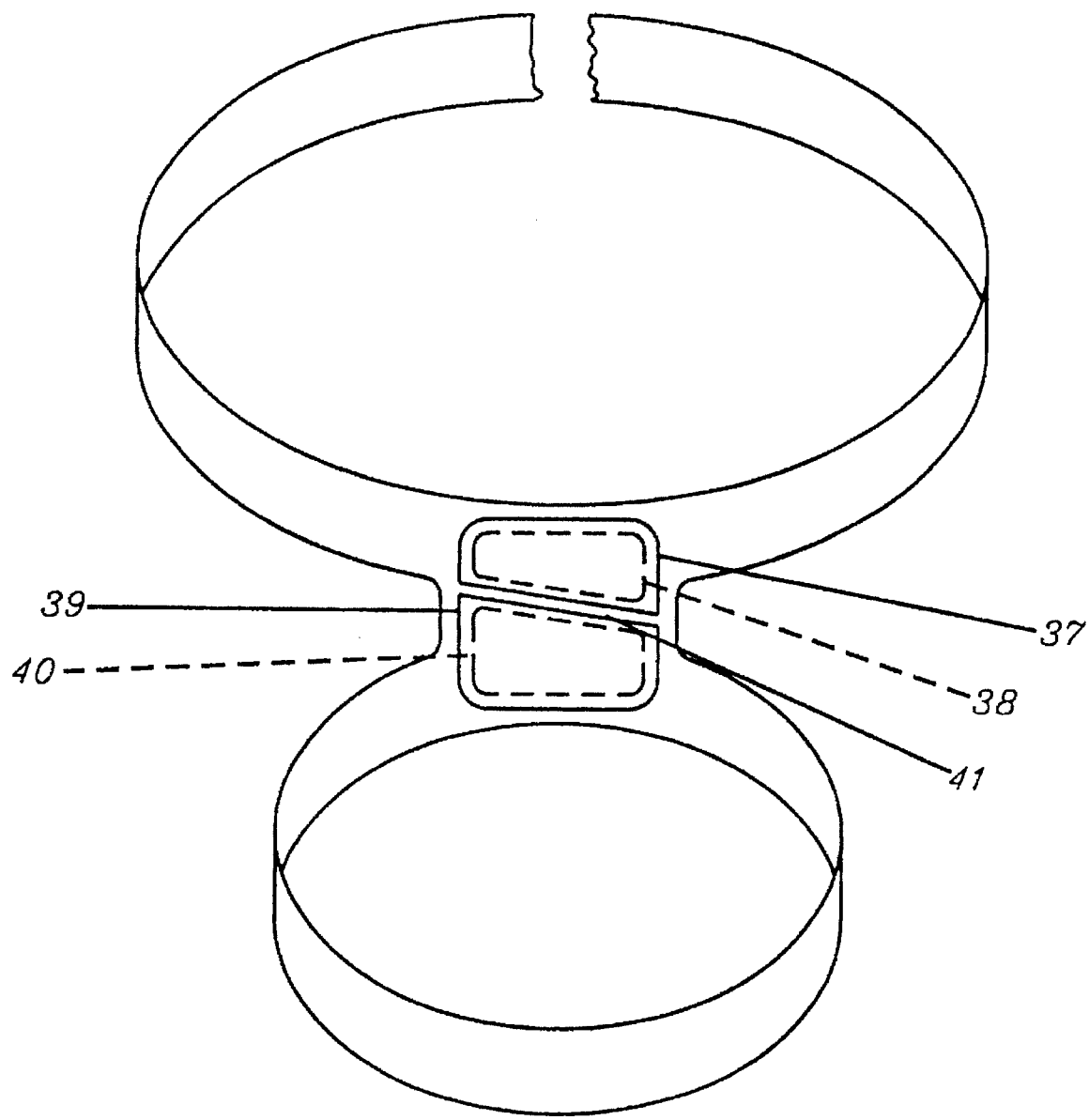

FIG. 16. Shows a unit similar to the one in FIG. 11 except this unit uses a combination of two balloons.

Figure 17:
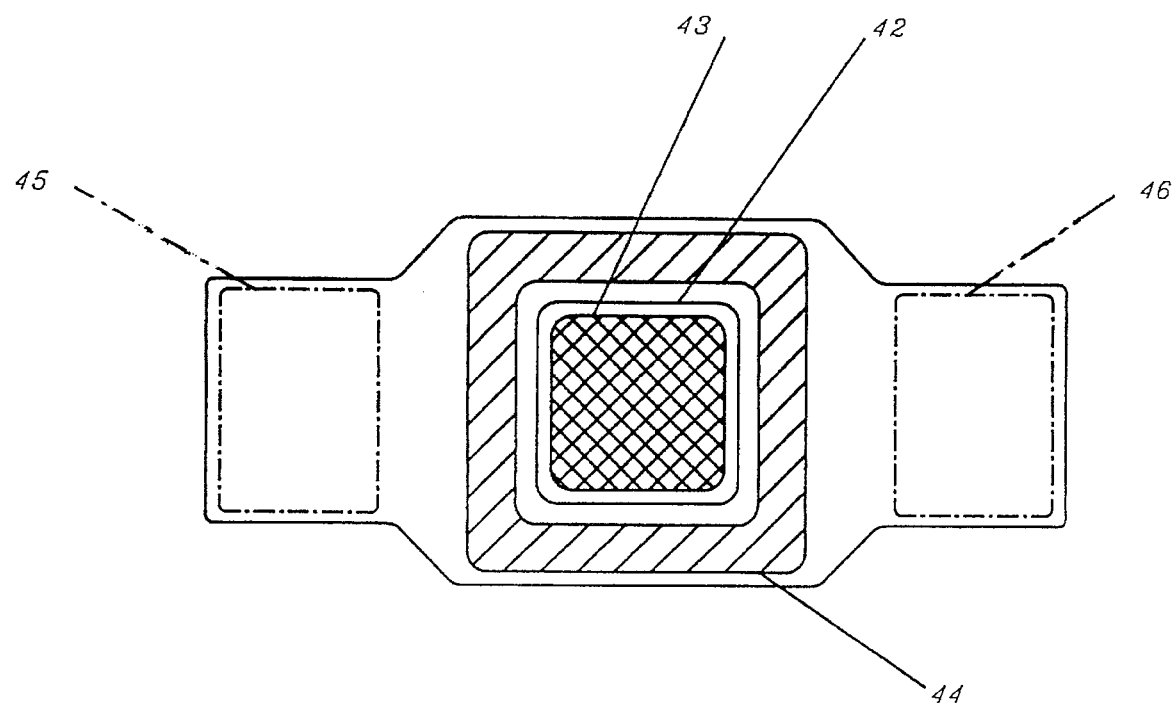

FIG. 17. Shows a unit with a band of adhesive around the center piece of this unit.

Figure 18:
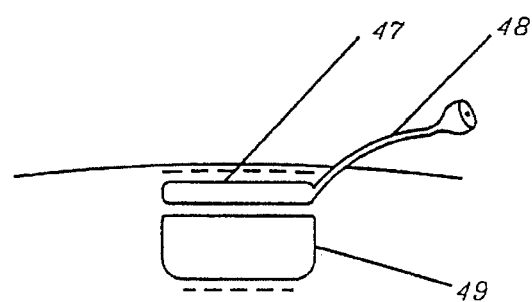

FIG. 18. Show the cross-cut view of a unit with two balloon on it.

DETAILED EXPLANATION OF THE FIGURES

FIG. 1. This figure shows the front view of a bleeding prevention unit, and is to give a general idea about it. This figure shows a support piece 1 which will hold the whole unit in place. This support piece has the clear balloon 2 on its lower surface; the front of this balloon has a layer of adhesive marked at 3 shown with a dotted and dashed line. The end pieces of the support has a film of adhesive marked at 4 on the right and 5 on the left side. These balloons will have one flat shape towards the support and the other surface will bulge out but will still have a rather flat front surface similar to the one shown in this figure, although different shapes are also mentioned in the other parts of these texts.

FIG. 2. This figure shows the cross-cut view of the unit shown in FIG. 1. In this figure the support piece is marked at 1 and the balloon at 2. Again the front of this balloon has a layer of adhesive marked at 3 with a dotted and dashed line. The end pieces of the support have a film of adhesive marked at 4 in the right and 5 on the left side. In this figure the front of this unit has a protective layer marked at 6 in the right and 7 on the left side which will be peeled off before use.

FIG. 3. This figure shows the from view of a bleeding prevention unit similar to the one shown in FIG. 1, except this unit also has a piece of rigid, clear plastic shown by a dotted line at 8 and the from of this clear, rigid piece has a layer of adhesive marked at 9 shown with a dotted and dashed line. The rest of the unit is very similar to the one shown in the previous model.

FIG. 4. This figure shows the cross-cut view of the unit shown in FIG. 3. In this figure the clear, rigid, plastic piece is again shown as a dotted line at 8 and the layer of adhesive is marked at 9 with a dotted and dashed line. The front of this unit is covered by a protective layer which has the function of keeping the surface of the unit clean and sterile as well. This layer is shown by a dashed line and will be peeled off before use.

FIG. 5. This figure shows the cross-cut view of a unit which is similar to the unit shown in the previous figure of 1–2. Except this unit, also has a pad of gauze in front of the balloon which is to absorb the secretions and blood from the wound. The front surface of this gauze pad is covered by a layer of adhesive which will allow the unit to stick to the skin and be stable. Since the adhesive is over the gauze pad it will have openings that will allow the secretions to go through so that importantly the blood, secretions from the wound, as well as sweat will be absorbed although the unit will still be stable on the wound site and will keep the wound area stable as well. The gauze pad will be clear if possible. In this figure the gauze pad is shown at 10 and the adhesive layer at 11 shown with dots and dashes.

FIG. 6. This figure shows the cross-cut view of a unit which is similar to the unit shown in FIG. 5. Except this unit also has a clear, rigid piece of plastic shown at the dotted line 13 which will stand in front of the balloon and under the pad of gauze. This is to allow a special impression to the wound to be given as well as the unit to be able to absorb the blood and secretions from the wound site. In this figure the gauze pad is shown at 12, the piece of plastic at 13, and the adhesive layer at 14 is shown with dots and dashes.

FIG. 2. This figure shows the cross-cut view of a unit with sensor leads inside the gauze pad, which are designed to cause an electrical circuit to be activated if bleeding occurs and the blood reaches the space between the electrodes inside the gauze pad. In this condition the presence of the blood between these electrodes due to its physical and chemical components will cause the electricity to pass through the space between the electrodes M and N, causing the electrical circuit to be complete. This electrical circuit per se after amplification and changes may cause different functions to occur such as an alarm to be functional and other pre-designed actions or functions will occur by the use of different systems such as the use of computers, mini computers, and the use of different mechanical means such as air pumps, etc. In this figure the support piece is marked at 15 and the gauze pad at 16. The cross-cuts of the circular sensors are at M & N.

FIG. 8. This figure shows the cross-cut view of a unit which is similar to the previous model shown at picture 130. Except in this figure the upper electrodes M has a circular shape with a curved edge toward the lower electrode N and also the electrode M does not have an opening in its center so that if bleeding occurs and the blood reaches this area, it will be directed toward the lower electrode N in order to make the electrical conduction more possible. The center of the lower electrode N has opening 19 to allow the blood to go through and reach the space between these two electrodes. Besides, the front of the gauze pad has a layer of perforated non-permeable layer marked at 17 which can be soft or rigid and will stick to the skin by the adhesive in front of it. This non-permeable layer will prevent the sweat of the skin from reaching the gauze pad as well. The center of this layer has an opening 18 in its center which will be shaped to fit the shape of the wound and to allow the blood to be absorbed by the gauze pad, causing the electrical circuit to be functional. This spot may be covered with a thrombogenic material such as gel foam or collagen in order to facilitate coagulation of the blood.

FIG. 9. This is an schematic figure in order to show how the bleeding detection system will function. In this figure the upper electrodes M are shown and it is a larger piece which will cover the lower electrode N here shown as a dashed line. The center of the lower electrode N has the opening 19 to allow the blood to go through and reach the space between these two electrodes. These electrodes are then connected by wire to a mini computer symbolically shown at 20 which will analyze the signal and may amplify it. It will then start pre-designed actions such as causing an alarm to sound, the patient to be informed, the patient to receive directions of what to do, an electrical pump to be functional in order to inflate a balloon or other informative or therapeutic actions to be taken. In this figure the electrode M and N are shown, the mini computer is marked at 20, the alarm inside it 21 and the battery at 22. This unit may also have a bedside-held button or a control unit so that an informed patient can press the button or use the control unit in order to make the automated system inflate the balloon and apply pressure. The patient may also use the control unit as part of relaying information to the medical staff as well by informing the nursing station via a proper network.

Importantly, the gauze between the electrodes may be treated with certain chemicals or materials in order to influence, exaggerate or modify the effect of the blood in the area for a better chemical, electrical or physical detection. Also, in different models these chemicals may be changed to allow different secretions to be identified such as secretions from wounds, amniotic fluids, etc. The sensor method may also differ; it may use any sensors: physical, chemical, optic, etc., in order to identify or modify the signals.

FIG. 10. This figure shows the cross-cut view of a unit which is similar to the previous model shown at picture 9. Except this unit also has a balloon 23 on it protected by a support unit 24. Also the balloon has an inflation port 25 which allows the tension of the air or the fluid inside the balloon to be adjusted. The support unit will go around the wound and may be stuck on the skin or to be wrapped around it. In some models it may use some bands of adhesive material as well as being wrapped around the area.

FIG. 11. This figure shows the general view of a unit which is to be used in the groin area and after cardiac catheterization. This unit is basically made from a clear, non-stretchable support piece in front shown at 26 which has one upper and one lower strap system in order to allow this unit to be held in place securely. This unit also has a balloon which will allow pressure to the wound to be applied. In some models a clear, rigid piece will be placed under the balloon in order to prevent the balloon from bulging outside. Alternatively, the support will be rigid enough to do so. In this figure, the support is shown at 26, the balloon at 27, and the rigid piece at 28. The upper strap 29 is to go around the belt area and the lower strap 30 is to go around the upper thigh in order to keep this unit in place safely.

FIG. 12. This figure shows the cross-cut view of the unit shown in FIG. 11 which shows only the balloon area. In this view the support piece is marked at 26, the balloon at 27, and the rigid piece at 28.

FIG. 13. This figure shows the cross-cut view of the unit which is similar to the one shown in the previous figure of 11–12. Except this unit has a piece of semi-rigid or rigid, preferably clear piece of plastic on its front in order to allow a particular impression to be used against the wound. In this view the rigid piece in marked at 31.

FIG. 14. This figure shows the cross-cut view of the unit which is basically similar to the one shown in FIG. 13. Except this unit also has a layer of adhesive film on its from in order to allow the unit to be stuck on the wound site in order to further stabilize the wound as well as having an effect on the stability of the unit as well. This layer will be protected by a removeable layer that will be peeled off before use [not shown in this figure]. In this picture the rigid piece is shown at 32 and the layer of adhesive at 33.

FIG. 15. This figure shows the cross-cut view of the unit which is similar to the one shown in FIG. 14. Except this unit has a layer of gauze pad in its front on the surface of the rigid plastic piece. This gauze pad is to absorb the remainder of the blood and the secretions from the wound or the sweat from the skin. The from of this gauze pad will be covered by an adhesive which will make this unit stick to the skin and hold the wound area securely. It will also allow the secretions to go through its small openings to reach the gauze pad and to be absorbed. This fill of adhesive may be similar to commonly used adhesives or it may be made from any kind of proper adhesive that may be made in the future and can be used in this area. In this picture the rigid piece is shown at 34, the gauze pad at 35 and the layer of adhesive at 36

FIG. 16. This figure shows a unit similar to the one shown in FIG. 11. Except this unit uses a balloon that is made from combinations of two balloons (37 and 39) that have a common oblique border 41 which will fit the groin line of the user. Each balloon also has two separate clear, rigid pieces of plastic (38 & 40) in order to prevent the balloon from bulging out if there is such a possibility. This unit also has the advantage that it can be used in cases when the protection of the lower abdomen and the upper groin area is needed. This unit will allow the person to bend his hip joint as well. Importantly, the different models of the balloons, the gauze pads and the rigid pieces for the front, etc., which were mentioned for the groin model mentioned for the previous groin model will also apply for this model as well except that it has to be modified to fit this model.

FIG. 17. The purpose of this figure is to show the band of adhesive around the center piece of these units which is to seal the area and to prevent the blood to leak outside. By doing so this unit will prevent blood loss and the stasis of the blood may start the bleeding process and to stop further bleeding. This figure shows the front view of a unit that has a pad of gauze in its front as well as a band of adhesive around the border of the balloon and the gauze pad. It is to give a general idea about such a model. In this figure the balloon is marked at 42, the gauze pad at 43, and the band of adhesive at 44. The adhesive layer on the surface of the end piece is on the left at 45 and on the right side at 46. Importantly, it is to be considered that when the gauze pad is treated by materials that can facilitate clotting such as gel foam, collagen or other chemicals it may cause a rapid clotting of the blood on the area which will prevent further clotting on its own.

FIG. 18. This figure shows the cross-cut view of a unit for the groin (this is a cut only in the balloon area) which is similar to the one shown in FIGS. 11–12. Except this unit also has a second balloon 47 under the first balloon 49 so that it will allow the second balloon to be inflated in order to provide a higher level of pressure in the wound site. This will be a back up unit for emergency use only. This fig shows the inflation tube of this balloon at 48 which goes thorough the support unit out. Importantly, this method may also be applied to the models that are shown in FIG. 16 so that a balloon will be on the rear side of those two balloons of 37 and 39 which can be inflated when needed. The shape of this balloon may be flat to fit the area well and to expand and fill the area and to press the wound properly. Please notice that the pictures which shows such models are not shown, primarily due to the fact that it will be a complicated, crowded picture, and especially since the applicant believes that the merit of such a unit is understandably discussed in the text.

Also, please notice the units that show a computer unit with the sensors and the groin unit's area [not shown again in order to avoid a crowded confusing picture and the applicant believes that the merits of such units are understandably discussed in the text]. Pictures will be provided if the examiner feels they are needed.

DETAILED EXPLANATION OF THIS INVENTION

Bleeding is one of the serious problems that occurs to the mankind. It causes concern, fear, weakness and if it is severe and continued it will kill a person in a short time. Therefore, bleeding is to be stopped in almost every occasion.

In general, cuts, wounds and injuries are the main causes of the bleeding; however, during medical procedures in which a vein, an artery or an inner part of a human being or animal is cut can be of a main cause of bleeding as well. Procedures such as cardiac catheterization, angioplasty, insertion of the intra-aortic balloon pump, insertion of catheters for monitoring pressure by arterial or venous lines, angiography of the brain vessels or extremities, insertion of wires or tubes such as pacemaker wires, electrophysiologic studies, insertion of large IV lines, or similar procedures all may cause bleeding in the wound area which can be severe and lethal. This is also true in a patient who receives certain medications such as anticoagulants: heparin, Coumadin and very powerful thrombolytic agents and had a cut or procedure performed as well. The leakage of the blood outside and in the vicinity of the procedures may also occur; trauma and injury to the wall of the vessels happen and cause not only blood loss but also changes in color and shape of the area, so called echymosis, hematomas and damages such as A-V fistulas. Besides the physical problems mentioned above, the psychological reaction and concerns of the patients, their relatives and the medical staff are all important as well. These issues come one after another and should be prevented and treated. For these reasons this applicant along with many other inventors has introduced units that will allow the initial bleeding in such cases to be stopped. However, another problem which has caught the attention and the interest of this applicant is the cases in which the initial acute bleeding was stopped by various means and the patient's wound appeared to be stable. In one case the patient was ambulated; however, about 3.5 to 5 hrs after the procedure, the patient vomited and developed bleeding on the wound site. Importantly, this was a period in which the patient appeared to be stable and ready to be discharged home. This was quite alarming since if the patient was discharged, he would have been out of the hospital and not under medical care. As mentioned earlier in one case the patient was already ambulated and appeared to be stable.

Such an event gave the indication to this applicant that the danger of bleeding may not be over even if the patient is clinically stable and was ambulated 3.5–5 hrs after the procedure. This was a set back for the hope that stable patients could be discharged from the center earlier as soon as they were stable enough to be ambulated without bleeding. This was an important issue since if there is any indication of bleeding then we as physicians would not discharge such patients early. This will cause a prolonged period of observation which is not only costly to health care but is also very uncomfortable for many patients and delays their trip home. In many cases this is difficult since it will extend into the night hours and in winter it may get dangerous as well.

Such an observation made this applicant introduce this for the prevention of such a problem. In this method, the applicant introduces a unit that due to its pressure producing unit will provide a mild to moderate degree of protection to the wound site. Importantly, some models of these units are also capable of providing even more protection in the wound area if needed. The applicant's observation has given him the idea that in this particular stage only a partial application of pressure to the wound will be helpful enough to prevent bleeding; this unit is designed to do just that. These units will use the same basic ideas that this applicant has previously introduced to USPTO for prevention of bleeding in the initial stage of such procedures (except one model which included special shorts and was to be used after the initial stage was over). For this reason the applicant respectfully requests the prior information to also be considered part of this application as well.

The makeup of these units. Basically, these units will be made from a non-stretchable support unit which will be resilient enough to prevent expansion of the balloon outwardly or will support a pressurizing method. Although in some cases the unit may be made from elastic materials to support the unit or it may have elastic components as well. In such elastic cases the unit will have a limit that will expand and then it will have a non-stretchable piece as well. This non-stretchable support unit will be shaped to fit the area and the need. It will hold a balloon or a pressuring unit in the wound site in order to press the wound and counteract the forces that may cause bleeding. In this stable stage such forces can be a severe cough, vomiting, straining, heavy activity, etc. Even though many forms of pressurizing units may be used with these units, in these models mostly the balloons will be utilized in order to apply such pressure to the wound. In general, the pressure to the wall of the vessel from inside will face the pressure from the tissue around the vessel as well as the added pressure from the balloon held in place by the non-stretchable support unit. Therefore, this will be an added pressure by this unit to prevent oozing and bleeding from the wound. Importantly, in these units another mean will also be utilized to intensify their effectiveness, which is the use of an adhesive layer to the front of these units in order to hold the edges and walls of the wound together. This will naturally also pull the tissue under the skin toward each other and will hold them together closely, which the applicant believes will be helpful in preventing the bleeding. Therefore, now the unit will be even more effective when the adhesive layer will be functional as well. The adhesive layer will play another important rule as well it is to hold this unit in place securely and to prevent it from being displaced which is understandably important in such cases. Such a displacement and shifting of the unit away from the wound site may occur due to ambulation, and dressing of the patient which is needed and encouraged in this stage. The support unit will be held in place by being wrapped or strapped around the wound site. However, the straps or the body of this unit may further include bands or strips of adhesives in their edges in order to make for stronger stability. Importantly, beside having a film of adhesive on the front face, the balloons may also have a piece of semi-rigid or rigid plastic or waxy material in order to give more stability and shape to the wound. These balloons may even have a pad of gauze to absorb the secretions in the area as well.

Therefore, in general the unit will have the following components:

1. A non-stretchable support unit such as the one shown in FIG. 1 at 842A which will be shaped to fit the anatomy of the area and will have the means to be fixed in the area to support the pressurizing unit. The center of this piece will be made clear in order to allow the condition of the wound side to be seen. In simplest form the support unit will be made to be like a band aid that can be used to prevent bleeding in small wounds; however, in other areas (like the groin) it will have a special shape to fit the area properly and securely. The support unit will be made from a non-stretchable material although it may also be made from an elastic material that will have a limit that it can be stretched so that finally will act like a non-stretchable material. It may be made from polymers such as vinyl, natural materials such as cotton fabric, or combinations of the natural and synthetic materials. The support unit may have a soft lining in order to make it comfortable for the patient. Importantly, when the end pieces or the borders of these support units have a layer of adhesive to stick to the skin, they may be made to have a series of holes or a porous make-up in order to allow the sweat of the skin to pass through, and the skin to breathe and be comfortable. Importantly, the support unit may have bands or straps designed to allow the unit to be held in place as securely as needed. For example: in the groin area it will have a strap to go around the belt area and another one to go around the upper thigh. In some models this may be modified to have a band or a strap to go around the neck in order to hold the unit in place more securely and prevent it from dropping down in a standing position. Also, the unit for the sub-clavian area may have a band to go around the chest and another to go around the shoulder area. The units for the chest and abdomen may also have a band or strap to go around the body or chest and another one to go around the neck to keep it in place securely. Therefore, the straps and bands will have different shapes and numbers in order to hold the unit in place securely.

2. A pressurizing unit. This will be a unit that will be supported by the support unit and it will produce pressure in order to press the wound site to prevent bleeding. This part may be made from different means such as:

a. Balloons (one shown at 2 FIG. 1) that can be inflated with air or fluid. These balloons may have different shapes, forms, and sizes to fit the need of the area. In general, they may have a cylindrical or a prism shape in which one of its flat faces will face and attach to the support unit and the other face will face the wound. Or it may have one flat face that will be attached to the support unit and its other face will bulge out to have a rather flat or a mildly curved pre-designed front wall to face the wound. These will be soft to conform and allow a mild to moderate pressure to be applied to the wound although the degree of the pressure inside the balloon, the softness of the balloon, the thickness and consistency of the wall of the balloon all may vary in different models in order to satisfy different needs. The other possible shapes of these balloons are mentioned and explained in the other parts of this application. They can be made from combinations of the balloons in order to allow different areas to be pressed differently. For example, a circular balloon in the center and a doughnut-shaped balloon around it will allow the center of the wound to be pressed differently from the peripheral area of the wound. In the groin area, it will allow one balloon to press the upper groin and the other one to press the lower abdomen area. This method will also allow one balloon to press the wound and the other one to be used for application of a higher pressure if the wound started to bleed. The balloons may be precharged or inflatable. The balloons may have different shapes: they may be round, square, rectangular, oval-shaped or can have other shapes in order to fit the shape of the area and provide the needed pressure. In inflatable forms they will allow the unit to be inflated by a unit such as a hand held bulb or any other means that can inflate these balloons properly. The consistency of the wall and the nature of these balloons may be different as well. The inflation port of these balloons will accept an inflation unit and may have different kinds of valves including a one-way valve and a three-way stopcock. Due to the importance of these balloons there will be a further discussion later in the text.

b. A pressurizing unit such as one made from a spring to be in the shape of a cake. This piece will have proper shape, size, and nature and will be placed under the support unit to cause pressure in the wound site. This unit may have a screw connected to the support or a handle in its rear surface in order to allow the tension of the unit to be adjusted. The support piece for the spring may be made to be clear in order to allow the wound to be visualized.

c. A screw system. This will be a properly shaped and sized screw that will be held securely by the support unit to press a rigid plate on the wound site. This tension in the area will be adjusted by movement of this screw. This method was shown in more detail in the previous applications of this applicant on D. Device 4, 5 and 6.

3. A clear, semi-rigid or rigid piece of plastic. (as shown at 8 FIG. 3–4) This piece will be made to have a proper size and curve to fit the wound site and to allow a special impression or application of pressure on the wound site. This piece may be curved or shaped to fit the anatomy of the area or the purpose of the impression to be applied. This piece may have a handle to allow it to be held comfortably; this handle may be broken later.

4. The unit may have a piece of rigid, clear plastic in the rear side of the balloon under the support unit (as shown by a dotted line at 28 FIG. 11–12) to prevent from bulging the pressurizing unit toward the outside.

5. The units may have a film or layer of adhesive on their front wall (as shown at 3 FIG. 1–2). This will allow the unit to be stuck to the skin on the wound site. This film of adhesive will be also protected and kept sterile by a protective layer that will be peeled off before use.

6. This unit may also have a series of pieces like bands or straps that will have a film of adhesive on their surface of their end in order to allow them to be stuck to the skin. This film will be protected by a protective layer that will be peeled off before use.

7. Some models of these units may have a pad of gauze (as shown at 10 FIG. 5 and 12 FIG. 6) on its front in order to allow the blood, secretions or the sweat from the wound to be absorbed. This gauze may be medicated in certain cases. The center of this gauze pad may have a small amount or piece of a thrombotic agent such as "Gel Foam" or "Collagen" in order to cause coagulation of the blood in the wound area to occur and to close the opening of the wound as well.

8. In some models the front surface of the gauze pad may have a layer of adhesive that will function to secure the wound and hold the unit in place securely in the same way that was mentioned earlier. However, it is to be noted that in this case the layer of adhesive will have a series of holes or it will stick to the front of the fabrics of the gauze pad so that it will leave a porous surface. This will allow the blood, secretions, or the sweat from the wound area to be absorbed.

9. The unit may use different kinds of inflators in order to inflate the balloon when it is needed. These may be by the use of inflation bulbs, syringes automated units, small gas containers, gas tanks, etc.

10. The pressure gauges may be of any type, nature and shape that can be used in these units. These may include commonly used manometers, mercury operated units or electronic units, etc., to allow the level of pressure to be known.

11. These units may use of automated sensors that will allow the bleeding to be detected as soon as possible. A model of these are shown in FIGS. 7–10. However, this may also be made from combinations of many sensors in different spaces and levels in order to allow detection of the bleeding and its expansion to be noted. This was originally introduced to USPTO by this applicant in his application of D. Device 2 which was applied on Dec 14, 1992, with Ser. #07/989,825 and is pending.

12. The use of mini computers will allow the functions of these units to be automated as much as possible.

13. Importantly, in some models such units have a pad of gauze in their from. The unit will be made to have a band of support unit around the gauze pad which will be covered with a film or layer of adhesive so that it will stick to the skin around the gauze pad in order to prevent blood from leaking out of the covered space if bleeding occurs. This will have a sealing effect in the area. These borders may be made to have a series of holes or a porous make up in order to allow the sweat of the skin to pass through and the skin to breathe and be comfortable.

14. A waxy material or material used in units called DuoDERM may also be used and can be placed as a layer in front of the balloons in order to stick to the skin at the wound site in order to give shape and hold the wound stably.

15. In general, the balloon will have a flat face that will face the support unit; its other face will bulge out, but will still have a rather flat pre-designed shape. It will be soft to conform to allow a mild to moderate pressure to be applied to the wound although the degree of pressure inside the balloon and the softness of the balloon may vary in different models in order to fit different needs. Naturally, the tension of the inflatable balloons may change with the inner pressure.

16. Importantly, the adhesive material of these units will be chosen to be friendly to the skin and not to irritate the skin or the wound, unlike present-day adhesives.

The support units will be held in place by the following means:

1. The use of bands or straps with a layer of adhesives at its end pieces. These will be made from vinyl, polymer, fabric or similar synthetic or natural materials and their combinations. The end pieces of these units where it has the adhesive areas may be made from a piece that is porous in order to allow for breathing of the air, sweat to pass, and the unit to be tolerated well. In larger units these straps will wrap around the limb or the body to keep the unit stable.

2. As mentioned above in no 13, importantly the support piece may also have a surrounding that is like a band around it which will be covered by a layer of adhesive so that it will allow the surrounding area to be stuck to the skin around the unit to make it more secure.

3. The support piece may have a series of strips of adhesive tapes that will allow the unit to be held in place securely.

As mentioned above some of these units may be made to have a mechanism that will allow an early detection of the bleeding to occur by the use of special sensors. One of these methods was previously mentioned in D. Device 2. In this method the gauze pad will consist of a series of electrodes which will be connected to a sensitive device which will detect the circulation of the electricity when it occurs and then will translate it to different signals. These electrodes will be placed in the area and preferably inside a pad of gauze so that in the absence of bleeding there will be no contact of electricity between these electrodes or sensors. However, if bleeding occurs, then the saturated gauze will cause the electricity to be conducted between the electrodes so that the electrical circuit will be complete to cause the alarm unit to sound. Such an electric signal may then be analyzed and modified by a mini computer in order to cause the needed favorable actions to be taken. For example, the patient, relative or the medical staff can be informed by: an alarm or voice to act properly, an electrical pump to inflate the balloon and prevent bleeding, a telephone to sound, etc. When the balloon is to be inflated the degree of such inflation will be determined by the preset level entered in the computer by the medical staff and, depending on the level of blood pressure of the patient, the amount of pressure which is needed to control the bleeding initially, etc.

Safety valves and pressure sensors will be used to prevent from over/under inflation of the balloon. An alarm may sound if the pressure drops from a preset level.

Importantly, the materials used in these units will be transparent or will have a transparent window to allow the wound site to be observed for better and easier care.

The inflation port of this unit will allow a bulb or a syringe to be used to inflate the balloon and a gauge to be utilized to measure the level of the pressure inside the balloon.

The prototype unit will be made from a clear, non-stretchable polymer such as vinyl that will allow it to be cut as well so that its size can be adjusted in some cases to fit the need better. This unit will have the balloon in its front and will also have a series of end pieces with a fill of adhesive on them in order to allow the end pieces to be stuck to the skin. These adhesive fills will be protected by a layer that will be peeled off before use. The front surface of the balloon will also have a layer or film of adhesive which will allow it to be stuck to the skin on the wound site. This fill of adhesive will also be protected and kept sterile by a layer of protective material that will be peeled off before use. Some models of this unit will have a piece of rigid, clear plastic in front to allow different effects on the wound site to occur: to protect the wound, to affect its shape or to give a special impression. Some models of these units may have a gauze pad in their front in order to absorb the blood and secretions. This gauze pad may be medicated in certain cases. In some models the front of the gauze pad may have a layer of adhesive as well. These units can be modified to be used in different areas of the body such as the forearm, the wrist, subclavian area or any other areas of the body.

The unit for the groin area.

This will be a unit that is modified in order to fit the need of the area and to be used after the initial stage is over. For this reason the following changes will be made.

1G. The non-stretchable support unit will be shaped to have an abdominal piece that will go around the belt area and an upper thigh piece that will go around the upper thigh area. These two pieces will be connected to a common front piece that will stand in between them on the wound and will support the pressurizing unit. The center piece will be made clear in order to allow the condition of the wound to be seen. The support unit may have a soft lining in order to make it comfortable for the patient. Importantly, the straps and/or the connection point of the straps to the front piece may be made to be adjustably connected in order to make the whole unit to be adjustable for the best use so that the unit can be placed on the needed spot. This may use any means of adjustability such as the use of adhesive material, Velcro, snaps, etc., so that the overall length of the straps can be adjusted. Also, D rings may be used in order to allow the strap to go through, make a U-turn and to be stuck, taped, snapped, velcroed on its own rear surface, or to use different methods of attachment for this purpose. Also, it should be noted that a larger rectangular, oval or circular unit with the balloon on its front may be used in this area to press the wound site although the unit with upper abdomen and lower thigh support will be more stable and secure.

2G. The pressurizing unit. This part will primarily be of the inflated balloon type, although a cake of spring or a lever system may be used to press a wound plate to the wound site. The balloon will be properly sized and shaped to fit the area. It may be made to be inflated with air or fluid. It may be precharged or inflatable. This balloon may have different shapes it may be round, square, rectangular or oval-shaped. A spring in the shape of a flat cake may also be used in order to press the wound site as well. The support piece for the spring may be made to be clear in order to allow the wound to be visualized. The spring may have a screw that will be fixed to the support system in order to allow it to be moved to adjust the pressure to the wound. A screw-lever system with a plate may also be used to press a rigid plate against the wound.

3G. These units may also have a piece of clear, semi-rigid or rigid plastic which will be shaped to allow special impression or application of the pressure in the wound site. This piece may be curved or shaped to fit the area and/or to provide a needed impression to the wound site. In rigid cases this piece may have a handle to allow it to be held comfortably; this handle may be broken later. In some cases instead of rigid pieces a waxy type material may be used to press the skin and also to stick to it due to its own structure or by having a film of adhesive in its front wall in order to support the skin. The use of units such as DuoDERM will also be helpful as well.

4G. In some cases the unit may have a piece of rigid, clear plastic in the rear side of the support unit to stabilize the pressurizing unit and prevent the pressurizing unit from bulging toward the outside.

5G. Some models of this unit will have a film or layer of adhesive which will allow it to be stuck to the skin on the wound site. This film of adhesive will also be protected and kept sterile by a protective layer that will be peeled off before use.

6G. This unit may also have a series of pieces like tabs, bands or straps around the front of the support piece that will have a film of adhesive on its surface in order to allow it to be stuck to the skin. This film will be protected by a protective layer that will be peeled off before use. Importantly, this piece may be like a band that surrounds all the circumference of the unit so that it will stick to the wound area all around in order to seal the area and prevent the blood from leaking out. The pieces that will be stuck to the skin may be made to have small holes or will be porous in order to allow the skin to breathe and the sweat to evaporate.

7G. Some models of this unit may have a layer of gauze on their front in order to absorb the blood, secretions or the sweat from the wound site. This gauze may be medicated in certain cases.

8G. In some models the unit may have a series of electrodes or sensors which will be placed inside a layer of gauze in certain distances from the center of the wound and will be connected to an electrical circuit so that if bleeding occurs the electrical circuit will be completed due to saturation of the gauze with blood and its components such as water, electrolytes, etc., which will cause conduction of electricity. This is to cause an alarm to sound for proper action or to initiate a computerized set of reactions to occur as well.

9G. In some models these units may be connected to a proper minicomputer that has a set of reactions based on certain events. For example, if the patient has bleeding the computer will start to pump an air pump in order to inflate a balloon and apply pressure to the wound area. The timing, the degree, and the course of such an inflation will be decided by the program and the related algorithm. This unit may be modified in order to measure the BP of the patient by having a ? calf in the arm and proper sensors in the artery site and then to relay the information to the computer to decide about the application of pressure on the wound site accordingly.

10G. Importantly, the connection of the straps to the from piece may be adjustable so that it will allow the unit to fit in the person easily. This may be done by any means such as the use of adhesives, adhesive tapes, Velcro (TM), snaps, etc. The straps may go through a D-ring, make a U-turn, and be attached to its own rear site. Adhesive means, Velcro (TM) means or any other attaching means may be used for this purpose.

11G. The balloon may be made to have a vertex so that it will fit the groin line and will have a face to stand against the lower abdomen and another face to stand against the upper thigh area. This was explained in D. Device.

In the following sections the reasons for using different parts and the important parts of these units will be discussed.

Why does the inventor introduce the piece of clear, semi-rigid or rigid plastic piece in front? These pieces will allow many beneficial functions in the wound site to occur such as protection of the wound from the unwanted shape of the balloons. For example: the balloons that develop a dome shape may not be beneficial to the wound since the dome of the balloon will press one area to a significant degree while the other areas of the wound may be spared. The dome may also be misplaced during movement or ambulation to press an unwanted area. Therefore, this applicant has introduced this piece which will allow for a desired type of impression on the wound. Some of these pieces may have a handle which will allow them to be handled easier. These rigid, plastic pieces may be shaped to match the shape of the wound area. Importantly, the front of the balloon may be made to be rigid as well or can have this small rigid piece stuck or incorporated on them.

These pieces may have a rectangular, circular, oval or similar shape. The commonly used sizes may be of about 5–6 cm by 5–7 cm. Importantly, different sizes may be chosen for a particular patient and also other different pieces may be placed or connected to them. These pieces may be used to shield or protect some parts, areas or the wound from the pressure of the balloon. These pieces will have special curves, domes or shapes to do this kind of job. The size, thickness, contour, relative thicknesses of the area and other characteristics of this unit may vary. In some models this piece may have a handle to allow its position and angulation to be controlled from a distance.

Why does the inventor introduce the piece of rigid, clear plastic on the rear side of the support unit? This is to prevent the pressurizing unit from bulging toward the outside of the unit which will be counter-productive and will take some of the balloon's volume away. Also, this is needed to support other pressurizing units such as spring or screw-lever systems to be functional. This piece may be curved and it may have different shapes such as a rectangle, circle, trapezoid, diamond to match the shape of the balloon. The sizes may also vary. The piece may be glued to the front surface of the support unit or in some models it may be simply placed between the balloon and the front piece. Importantly, when the rear surface of the balloon is made to be rigid, then the use of such a hard piece may not be needed.

Why does the inventor introduce a film or layer of adhesive in front of the balloon or the rigid front part? The applicant believes that bringing the edges of the wound together is important to promote healing and to prevent bleeding. Also, when the skin and related tissue around the opening is held tightly, it will have a sealing effect in the area and in the subcutaneous tissue and to some degree will prevent bleeding.

Why does the inventor introduce a series of pieces like tabs, bands or straps to be stuck to the skin? This is in order to hold the support unit on the skin more strongly and to further support the wound area. A band around the circumference of the wound will seal off the area and may prevent blood loss.

Why does the inventor introduce a layer of gauze in the front of these units? This is to allow absorption of blood, secretions and sweat from the wound site. Importantly, this gauze pad may be medicated in certain cases. For example: the use of thrombotic agents such as Gel-Foam or Collagen may promote the clot formation in the area if bleeding occurrs. The use of antibiotics may be beneficial in some cases. The gauze pads may have different sizes, shapes, and thicknesses as well. These gauze pads can be pre-medicated to allow faster usage. The thickness of these gauze pads may vary and they may have removeable pieces in order to allow their thickness to be adjusted to compensate for the wound area of the patient. This was introduced and explained in length in a previous application of this inventor called Daneshvar's device 7. This removeable piece may be a plastic piece with a thickness that will allow the thickness to be adjusted which can be very important. For example, in obese patients there is a depth in the groin area such that the regular balloons of these units alone may not be enough to compensate for this depth and create the required pressure in the area. Therefore, in such cases the use of a thicker gauze pad which also has a thick plastic body will be of significant benefit. It is important to notice that making thicker gauze pads by folding them has the problem of making a spongy unit that will not allow proper pressure to the wound area to be applied. For this reason, the inventor introduces gauze-plastic packages that are combinations of a plastic unit (with a different, or adjustable thickness) and a pad of gauze material so that their combinations will make a unique unit for this kind of use. Importantly, the use of the pieces of plastic (especially transparent plastics) will be of main interest since they will provide the ability of observing bleeding or other changes in the wound site. The size, shape, material, thickness, consistency, absorbency, thickness in different areas, coloring, chemical material, surface material and any other important characteristic of these gauze and plastic-gauze pads may vary in order to make a unit that will satisfy the special condition of the patient and the medical staff.

Why does the inventor introduce an automated alarm system? This is due to the fact that the applicant has observed that many of these patients are sedated for the procedures or have lost sleep and so after the procedure they are drowsy, sleeping and may not recognize the bleeding. Also, commonly the medical staff are busy and may not be able to observe a given patient continuously while bleeding may occur at any time and the delay in detection of bleeding can be very detrimental. Therefore, it will be of great advantage to have a system that alerts the patient and the medical staff to the bleeding as soon as it occurs. This process will speed up the preventive measures and will diminish the blood loss.

Why does the inventor introduce computerized units? This is due to the fact that computer technology is now so advanced that a mini computer can accept and hold a tremendous amount of information and follow an algorithm rapidly in order to make very complex calculations in a very short time. Therefore, they can be used to speed up a reaction in these conditions and can be of great help to the medical staff. They can alert to medical staff and initiate inflation of balloons, etc. They will automatically schedule the inflation. For example, it will be easy to set the computer to cause a pump and series of sensors and valves to keep pressure inside the balloon for a certain period of time and then to drop it to another level for another period of time and to inform the staff if there is a significant change. It will allow any accidental deflation of the balloon to be known quickly, etc. It will also allow the balloon to be inflated to a desired level if the patient has bleeding. The timing, the magnitude of inflation, and the course of such an inflation can be set by the medical staff and by use of the program and the related algorithm. This unit may also be made to measure the BP of the patient and decide accordingly as well.

The advantage of adjustability. The connection of the straps to the from piece may be made to be adjustable so that it will allow the unit to fit the person easily. This can be done by many different means. For example, the strap may go through a D-ring, return and be attached to its own rear site. Adhesive means, Velcro (TM) means or any other attaching means may be used for this purpose as well in order to allow the length of the straps, their connection spot together, or connection to the front piece to be adjustable. This is of significant importance since the applicant has noted how the patients are different and how the unit needs to be adjusted in order to make them fit different patients.

The lower strap of this unit may have a U shaped rigid piece in order to prevent from a tourniquet effect. In some models the lower strap will be made to have a removeable U-shaped unit attached to them. This is in order to prevent the lower strap of these units from making a complete tight band around the upper thigh, which rarely may act like a tourniquet and prevent the blood from returning to the body. This causes a problem. This is due to the fact that a similar condition was recognized in one patient during one clinical study of this applicant. Therefore, in order to prevent such an occurrence the applicant has made a U-shaped piece from a rigid plastic such as acrylic that is to stand under the lower strap in order to prevent from the tourniquet effect. This U-shape piece will have lower corners that will not press the body of the person and thus will prevent the creation of a tourniquet effect by the lower strap. These pieces may be made in many different forms: one model may be made from a single U-shaped piece or from combinations of two pieces that will be connected to each other to make such a unit. This two-piece model will allow the width of the unit to be adjusted. The length of the upper arms of these units may vary: in some units they may be long enough to allow direct connection of the lower ends of the front unit to the end sites of this U-shaped piece and to practically eliminate the need for lower straps.

This U-shaped piece may also be made in the shape of a flat bendable canal that will accept and hold the lower strap inside it and allow this piece to be pulled to the sides easily without the patient moving his/her body. In some models the shape of this canal may be similar to the wall of an accordion so that it will allow the wall to be bent easily. The front surface of this unit then will have a softer cover to avoid hurting patients. In some cases this U-shaped piece may be reduced to be only a properly sized and shaped rigid, flat piece that can be placed inside the lower strap in order to perform the job of the U-shaped unit to a reasonable degree. This piece may also be in the shape of a flat tunnel to allow the strap to go through. These units will be made in different sizes to match the size of the users, such as small, medium and large sizes.

Explaining different models of these units. This unit will be made in different models to match different needs in different areas. In its prototype model as shown in FIG. 1 the unit will be made from a clear, non-stretchable, support unit that will have a clear balloon in its front covered with a layer of adhesive. This unit will be held in place with the use of end pieces that have a layer of adhesive that will stick to the skin. And/or the unit will have straps that will go around the body to keep it in place securely as well. The front surface of this unit may have a rigid, semi rigid piece of plastic to cause a special impression to the wound. The front surface of these units will be protected and kept sterile by a removable layer that will be peeled off before use. These units may be made in different sizes from a band-aid size to larger units and can be used in different areas of the body to prevent from bleeding.

In some models these units will be further fortified by use of a pad of gauze in its front. This is to absorb the blood, secretions or the sweat from the area. The front surface of this gauze may be free or it may also have a layer of adhesive to allow the unit to stick to the skin in order to stabilize it and to be more stable as well. In such a case then the adhesive will have openings that will allow the secretions to go through and to be absorbed by the gauze pad.

As mentioned above and shown in FIGS. 7–10 some models of these units will also have a mean to detect bleeding in the area. This will be done by the use of special sensors which will be placed inside the gauze. One model of this is shown at FIG. 7. In this model a series of sensors are placed inside the gauze pad. This method if the bleeding occurs will be absorbed by the gauze pad. When the blood reaches the space between the electrodes of the sensor then the presence of the blood between the sensor leads due to its physical and chemical components will cause the electrical circuit to pass through the space between the electrodes M and N. This will cause the electrical circuit to be complete. This electrical circuit per se or after amplification and changes will cause an alarm to be functional and other pre-designed actions or functions to be taken by the use of different systems such as the use of computers, mini computers, and other means and methods to cause favorable steps to be taken. This is believed to be very important since it will provide a mean of safety and will allow early detection of bleeding or secretion of certain fluids to occur. In these models the pads and leads will be disposable but the minicomputers will be reused and there will be connections means between the leads and the computer.

The model shown at FIG. 8 shows the cross-cut view of a unit which is similar to the model shown at FIG. 7. Except in this figure the upper electrodes M has a circular shape with a curved edge toward the lower electrode N and also the electrode M does not have an opening in its center so that if the blood reaches this area it will be directed toward the lower electrode N and will make the electrical conduction more possible. The center of the lower electrode N has the opening 19 to allow the blood to go through and reach the space between these two electrodes. Also, the front of the gauze pad has a layer of perforated non-permeable layer marked at 17 which may be soft or rigid and will stick to the skin by the adhesive in its front. This non-permeable layer will prevent the sweat of the skin from reaching the gauze pad. The center of this layer has an opening 18 which will be shaped to fit the size of the wound and to allow the blood to go through, be absorbed by the gauze pad, and make the electrical circuit functional. Such shaping of the opening can be originally made or it can be achieved by cutting the non-permeable layer in a certain shape before use. This non-permeable layer may have perforations to allow such a cut to occur easily. FIG. 9 schematically shows how the bleeding detection system will function. In this figure the upper electrodes M has a size which covers the lower electrode N here shown as a dashed line. The center of the lower electrode N has the opening 19 to allow the blood to go through and reach the space between these two electrodes. These electrodes are then connected by a wire to a mini computer symbolically shown at 20 which will analyze the signals, modify them and then will start pre-designed actions such as causing an alarm to sound, patient to be informed, the patient to receive directions of what to do (either in written form or by sound), a pump to be functional to inflate a balloon or other informative or therapeutic actions to be taken. This unit may also have a bed side held button or a control unit so that an informed patient can press the button or use the control unit in order to make the automated system to inflate the balloon and apply pressure. The patient may also use the control unit as part of relaying information to the medical staff as well by informing the nursing station via a proper network.

Importantly, the gauze pad (which importantly may be made from different fabrics and materials) between the electrodes may be treated by certain chemicals or materials in order to exaggerate or modify the effect of the blood in the area for a better chemical, electrical or physical detection. Also, in different models these chemicals may be changed to allow different secretions to be identified such as secretions from the wound, amniotic fluids, etc. Importantly, the sensor method may differ in different models; it may use any types of sensors; physical, chemical, optic, etc, in order to identify or modify the signals. FIG. 10. This figure shows the cross-cut view of a unit similar to the model shown at FIG. 7. Except this unit also has a balloon 23 on it protected by a support unit 24. This balloon may be precharged or it may have an inflation port to allow the tension of the air or fluid inside the balloon to be adjusted. The bands or the straps of the support unit will go around the wound and may be stuck on the skin or be wrapped around it. In some models it may use a series of bands of adhesive to allow it to be stuck on the skin more securely. These will be bands connected to the periphery of the center of the support unit by having end pieces that have a film of adhesive to stick to the skin. In other models it may have a continuous band of adhesive around the circumference of the gauze pad that will allow it to be sticked on skin (as shown at 44 FIG. 17) in order to seal the area and prevent from blood leakage outside; it may also have the straps to allow it to be wrapped around the area.

FIG. 11. shows the general view of a unit which is to be used in the groin area after cardiac catheterization or similar procedures in this area. This unit is basically made from a clear, non-stretchable, support piece in front marked at 26 which has one upper 29 and one lower 30 straps in order to allow this unit to be held in place securely. This support unit allows pressure to be applied to the wound (which is commonly in the upper groin near the groin line) by different means such as the use of balloons, springs, a screw-lever system or by hydraulic means. Some models of this unit may have a clear, rigid piece shown at 28 FIG. 11–12 under the balloon in order to prevent the balloon from bulging outside. Alternatively, the support unit may be made to be adequately, rigid in the center to do such a job. The corners of this support unit will be connected to the straps. The upper strap will go around the belt area and the lower strap will wrap around the upper thigh in order to keep this unit in place securely. The connection spots between the strap system and the front piece marked at A, B, C, & D or in one or two spots in the length of strap marked at E, F, G & H of the unit may have means of adjustment in order to allow the length and possibly the direction of the straps to be adjusted easily. This may be done by various means with the use of sticking spots, press buttons, different snaps, or mechanical means. The D rings may also be incorporated in the straps in order to allow one end of strap to go through it, make a U turn, and to stick to its own surface by various means. Any other means of such adjustable connections may also be used in these areas. FIG. 10 shows the side view of the balloon of such a units for the groin [please notice for the sake of the figure's simplicity the whole unit is not shown]. Please notice that different balloon shapes may be used with these units such as flat balloons and balloons with one flat face and one bulging face, etc. The general shape of the balloons may be different as well. The consistency of the balloon may also vary in order to make different units for different uses. Importantly, the balloons will be made to be clear to allow the wound to be seen. The applicant has explained his reasons about the use of different balloons with different shapes and characteristics in his previous applications of D. Device 5 and Daneshvar's Device 7. In order to prevent redundancy he will not repeat the whole discussion here although he has made some remarks in this regard later in this text and keeps his right of using those logistics in this application as well. Importantly, in some models the front of the balloon may have a piece of semi-rigid or rigid, preferably clear piece in order to allow a particular impression to be used against the wound. Importantly, this piece may be made from a waxy type of material that will stick to the wound area as well as causing the area to be particularly pressed as well. (This waxy piece will stick to the skin due to its own characteristics or due to a layer of adhesive in its front). The center of this waxy material may have a small piece of gauze or thrombogenic agent in its front to face the wound. In some models the front of these balloons or the front of the rigid piece may have a layer of adhesive film in order to allow the unit to be stuck on the wound site. This is to play an important role first to hold the edges of the skin of the wound together and make it to heal sooner; secondly by holding the skin together it will also hold the related subcutaneous tissues closer as well which will have a beneficial effect on the stability of the wound and prevention of bleeding. Thirdly, this method will also hold the balloon and unit in the wound area more securely and will prevent it from being displaced during the movement of the patient which is expected and will be encouraged at this period. The adhesive layer will be protected and kept sterile by a removeable layer that will be peeled off before use. Importantly, although primarily the balloon will be attached to the support units, in some models the balloon may be separate. It may be placed on the wound site first and can then be attached to the support unit by the use of adhesives or attachment means.

FIG. 13 shows the cross-cut view of a groin unit in the balloon area. In this case the front of the balloon has the clear semi-rigid or rigid piece in its front marked at 31. The FIG. 14 shows a similar unit except the front of the rigid piece 32 has a layer of adhesive 33 to allow it to be stuck on the wound site. FIG. 15 shows a similar unit for the groin except the front of the balloon has a piece of clear, rigid plastic shown at 34 which also has a pad of gauze 35 on it. The front of the gauze pad is covered by the layer of adhesive marked at 36. This unit will allow the stability to be maintained as well as blood and secretions to be absorbed as well. FIG. 18. This figure shows the cross-cut view of another important model which is basically similar to the one shown in the previous figures of 11–12. Except this unit also has a second balloon 47 under the first balloon 49 so that it can be inflated in order to provide a higher level of pressure in the wound site. This will be a back up unit for emergency use only.

FIG. 16 shows the cross-cut view of a groin unit which will be basically very similar to the unit shown in FIG. 11. Except this unit uses combinations of the balloons 37 & 39 which have a common oblique border marked at 41. The line 41 will allow the balloons to bend toward one another along this line and will fit the groin line of the user. This kind of balloon combination is very important in cases in which the perforation of the artery is close to the groin line and there is a need for simultaneous protection of the lower abdomen and the upper groin area. This unit will fulfill this function. These balloons may have a small connection area between them so that only one balloon will be inflated in order to inflate both of them. The particular shape of these balloons will allow the person to bend his hip joint as well. Also importantly, these balloons may have another balloon that can be held on the line 41 and can function as a wedge if there is a need for the further pressure it can provide. This was introduced in the applicant's previous application of D. Device 3 in FIGS. 5, 6 and 7 [these will not be repeated here to prevent redundancy]. This third balloon may have a wedge shape or a rather flat shape and may be stuck or held securely to the side of these balloons by a strap that will be connected to the body of the support system of these units. The rear surface of the support of this third balloon may also have a rigid piece in order to allow it to create pressure in the area. Also importantly, the method shown in FIG. 18 may also be very effectively applied to the models that are shown in FIG. 16 so that a balloon will be in the rear side of balloons 37 and 39 which can be inflated when needed. The shape of this balloon may be flat to fit the area well, to expand and fill the area, and to press the wound properly. Also importantly, different models of the balloons, gauze pads and rigid pieces for the front, adhesive tapes, etc., which were mentioned for the groin models shown on FIG. 11 will also apply for this model as well except they will be modified to fit this model.

FIG. 17. The purpose of this figure is to show the general shape of the band of adhesive around the center piece of these units, which is to seal the area and to prevent blood from leaking outside. By doing so this unit will prevent blood loss and furthermore stasis of the blood in the area especially if it is exposed to thrombogenic material from the gauze which may start the clotting process and will stop further bleeding. This figure shows the front view of a unit that has a pad of gauze in its front marked at 43 as well as a band of adhesive around the border of the balloon and the gauze pad. This is to give a general idea of such a model. In this figure the balloon is marked at 42, the gauze pad at 43, and the band of adhesive at 44. The adhesive layer on the surface of the end piece of this unit on the left is shown at 45 and on the right side at 46. Importantly, it is to be considered that when the gauze pad is treated with a thrombogenic material such as Gel-foam or Collagen it will facilitate clotting of the blood on the area and prevent further bleeding.

Importantly, the computer unit may allow a connection between the patient's unit and a central unit to occur in order to monitor the patient by a central unit. Also, the computer of the unit may be connected to an arm piece that will allow the patient's blood pressure to be checked and the pressure of the unit to be adjusted based on this blood pressure. For example, if the patient's blood pressure is 7/67, the initial pressure of the balloon can be set at 17 level to stop initial bleeding. The computer will allow further steps to be taken as well.

Computer use and mini computers will extend the usefulness of these units many times and allow special functions to occur. For example, the use of mini computers will allow these units to be inflated in the beginning and then will have a program to follow the follow-up plan to keep pressure in a pre-set level for a particular period of time and then to decrease it to a pre-set pressure and to keep this for a certain period of time, etc. If there is bleeding, the unit will tell the patient to rest and lay down in supine position and hold the unit properly in place. The unit will pump air into the balloon and will increase pressure inside the balloon to the previous level or a pre-designed level which was effective in order to prevent bleeding. This unit may also be more effective by the use of sensors such as a doppler or pressure sensitive sensors; the noise detector or pulse detector sensors can be used for checking the pulse of the patient in his/her lower extremity and alert any alarming drop in pulse volume. The patient's blood pressure can be monitored as well and the changes can be given to the computer to adjust the pressure of the unit if needed. All of these functions can be done with the use of mini-computers which are now so powerful that they can keep a tremendous amount of information in their memory and can analyze them and work faster than the human's mind. When such units are then properly programmed they can be of great help to the medical staff and will decrease their job to a significant amount, and allowing them to be used in cases in which human input is needed.

Importantly, the applicant believes that it is also possible to incorporate the use of doppler technique in the groin units in order to find out possible changes in the venous return in the leg. This can be very useful in scientific studies as well.

The advantages of these units.

1. Basically, these units will be made from pliable materials that will allow the patients to tolerate activity easier.

2. These units will increase the chance of preventing bleeding due to their adhesive protective layer that will stick to the skin in the area.

3. These units will allow application of pressure to the wound site by the use of inflated balloons if the need occurs. This can be done by use of a single balloon or one front balloon and one reserve balloon in its back.

4. These units give the advantage of allowing the pressure of the balloons to be changed if needed.

5. Some models of these units will allow a sensor to detect the bleeding in the area and to give an alarm.

6. A clear balloon and a support system give the advantage of viewing the wound site without the need to open the unit.

7. The automatic units may also allow an automatic response to the pressure of the patient by a computerized system.

8. The flat piece in front will allow better control of the wound in many cases.

Some more discussion about the balloons.

Importantly, since the size of each patient and the anatomy of the area, the location and need of each wound may be different in different patients, different balloons are needed to allow the proper care to be accomplished in each and almost every case. Therefore, in general the characteristics of the balloons have to vary; these balloons may have different sizes, from small bubbles to big balloons. The thickness (when inflated) of the balloons may vary throughout as well; they may be thick in the center or some other areas, or they may have almost the same thickness throughout. The thickness of the balloon's wall may vary from unit to unit to match the needs of the area since some wounds need more pressure. The thickness and consistency of the walls of a given balloon may be different from one area to another of the same balloon. For example, a unit may have a thicker and harder rear surface than its front wall. The balloons may have a rigid area in its front to cause selective pressure in one particular area. The balloons may be filled with air or fluid.

Flat balloons may be used in some models; these will bulge in both front and back. They may be made to occupy the area between the support unit and the wound to make the units very stable. These balloons may be made in different shapes such as circular, rectangular, oval, etc. The balloons may be made to have a curved front and rear walls so that it will allow the balloon to expand on both sides so that overall, it can expand more to decrease the chances of rupture. This kind of balloon will be more useful in cases such as obese patients in which there is a need for significant expansion of the balloon in order to fill the space between the front support cover and the wound site in the groin. In some models an expandable balloon which has a flat front and rear wall, and a side wall that is similar to the wall of an accordion will be caged inside two rigid covers in which one stands on another so that with the inflation of the inner unit, the rigid covers will move away from each other to allow the wound area to be pressed. This model was shown in details in Daneshvar's Device 7 and has the advantage that it will eliminate the chances of perforation in the balloons and will make a rather solid unit. The shape of this unit may differ it will have the shape of a prism and its cross-cut view may be round, rectangular, oval, trapezoidal, etc.

These balloons may be pre-charged or may be inflatable. These will be connected to a gauge as well as an inflation unit.

The balloons will be shaped to match the shape of the area and fit the place well. In order to have the choice of having a proper balloon for a given wound, balloons with different shapes and configurations will be made. For this reason, the general shape of these balloons may be circular, oval, triangular, square, rectangular, rhomboid, irregular, doughnut or ring shaped. The ring-shaped models with openings on the side or center will allow the unit to be placed around a vascular sheath, an IV line or similar lines. Units with many openings can be used to fit the space between the IV lines or vascular sheaths. Units with differently-sized openings in their sides and units with different thicknesses in their course will allow them to be used in particular areas. Combinations of different shapes and sizes can be of help in a patient with different needs for control of his/her wound. Soft balloons may be used to be placed on the vascular sheaths in order to press the area between the sheaths and prevent bleeding in such an area. In one model a rectangular balloon -bag was changed by having the balloon's or bag's front and real wall stick to each other along an oblique line. This construction was made to leave an opening between the walls of the balloon so that the air could go through and made two almost different balloons connected to each other along that line. The use of such a balloon in the groin was very useful in allowing the person to bend his/her hip joint. This was introduced to USPTO in D. Device 2. Importantly, this model shows how balloons with different shapes may be made by sticking the walls of these balloons along different lines. Importantly, these may be made from more than one balloon as well. The balloons may be made from combinations of other balloons in order to allow different amounts of pressure to be applied and also to allow differential pressures to be applied on the wound as well. The combinations of balloons will allow differential pressure application on each side and also will protect one balloon from another if perforation occurs. Sometimes instead of balloons, bags of fluid or other liquids may be used and thus the bags may be used here with balloons. The balloons, bags and wound plates may have signs, signals, printed lines, shapes, configurations of any kind, or colors to provide information and facilitate their placement and use. The color of one area, part or surface may vary from one to another in order to provide means of transforming information to the users. These will be useful to show where they are to be placed and how to be used, etc. For example, a line may direct the user to position the balloon to stand over the imaginary line between the artery and the vein so that higher pressure may be applied on the artery.

In some cases these balloons may be chosen to be filled with liquid, fluid or gel.

To summarize, the balloons may have the following characteristics:

1. The balloons may be made to have one front balloon and one in the rear to allow it to be inflated if needed for higher pressure application. In such a case a flat inflatable balloon will be placed on the rear side of the front balloon so that the inflation of air-filled balloon will compress the air or fluid-filled front balloon toward the wound. A proper gauge may be connected to one of these balloons to allow measurement of pressure to be done. The front balloon may be precharged and the rear balloon can be inflatable.

2. The balloons are to be made from a clear polymer such as clear vinyl, rubber, polyurethane or similar materials.

3. The balloons may have pre-designed shapes to match the shape of the wound area such as subclavian, wrist, forearm, groin, etc.

4. The general shape of the balloons may be circular, oval, triangular, square, rectangular, rhomboid, irregular, or their combinations.

5. The balloons may have different sizes, from small bubbles (for band aids) to the big balloons.

6. The overall thickness of the balloons when inflated or their diameter from front to back may vary throughout as well; they may be flat, thick in the center or some other point, or may have almost the same thickness throughout.

7. The thickness of the walls of the balloons or the material used to make the balloons may vary as well. This is to allow the unit to match the need of the area since some units and areas need more pressure than others.

8. The thickness and consistency of the wall of a given balloon may differ from one area to another. For example, a unit may have a thicker or more rigid rear wall than its front wall, or the center of the front wall can be thick and flat to act like a rigid front piece, etc.

9. The balloons may also have a pre-shaped, rigid or semi-rigid dear piece in their front. Such a piece may have any size and shape such as triangular, square, rectangular, circular, oval, rhomboid, trapezoidal, irregular, etc. This is to cause a special effect on the wound site.

10. The balloons or bags will be transparent to allow observation of the underlying wound area to be done easily; however, they may also be made in different colors.

11. The surface of the balloons or bags may have signs, signals, printed lines, shapes and configurations of any kind to provide information and facilitate their placement and use. The color of one area, part or surface may also vary from the other in order to provide means of transforming information to the users and facilitate use.

12. Use of balloons or bags filled with liquid will give the opportunity for the application of coldness or heat to the area.

13. The balloons may have a means of connection to the wrap or the support part by having an area of adhesive, velcro, snaps or any other attachment means to allow connection of the balloons to the inner surface of the cover. This connection may be permanent or reversible.

14. Importantly, it should be mentioned that instead of one balloon, combinations of the balloons may be used for many various reasons so that one area may be pressurized while the other area would not be. Or one area could be covered by another balloon when a particular one is not enough. This technique will allow time and pressure differences between the inflation to occur which is important in certain cases such as pressurizing one zone of the wound more than the other or using a low level pressure by one balloon and higher pressure by another one as needed.

15. The balloons may be pressed against the wound by any possible means: mechanical, hydraulic, etc.

16. One model of these balloons may be made in the shape of a triangular prism. This balloon, when filled by air or fluid, can be used by the patient to be held in place on the wound site in the groin. If there is bleeding, the patient is to bend his/her hip joint in order to press the area. The surface of this unit may also have a gauze pad to stand in front of the wound. Such a unit may be used to press the wound during transferral of the patient to home by the car. This unit may have straps or bands to go around the belt and thigh area to hold it in place securely.

17. One model of these balloons has the shape of a rectangular balloon with its front and real wall stuck to each other along an oblique line. This may leave an opening in this line to allow air to go through to inflate both of the balloons at one time. This will make two balloons connected to each other along that oblique line. The use of such a balloon is more useful in cases such as groin wounds which will allow the person to bend his/her hip joint. Importantly, this model shows how differently shaped balloons may be made by sticking the walls of the balloon into different shapes.

18. These balloons may have hard, clear, plastic pieces of any shape attached to their rear surface with one or more handles on the sides in order to allow the position of this unit to be modified, tilted and controlled easily.

19. Importantly, the handle of these balloons may be made adjustable, removeable, bendable, twistable or easily broken away or cut.

20. A model of these flat balloons may have the shape of a ring or doughnut in order to be placed on a wound that needs to be dressed through the hole of the rings or has a catheter or sheath connected to it which does not allow the regular balloons to be utilized. In such a model the support unit will be changed and designed to allow for such a use.

21. A flat balloon in the shape of a horse shoe (or one like a circle with one open side) will allow it to go around a sheath or tube that is connected to the wound and would not allow a ring-shaped balloon to go over it. In such a model the support unit will be changed and designed to allow such a use to occur.

22. A softer flat balloon may be used to go over areas on the wound that does not allow other balloons to be placed on them, such as after angioplasty when the sheaths are in place.

23. A balloon with a flat, rigid, rear surface will allow bulging of the front wall to occur.

The hydraulic system may also be used to press the balloons on the wound as well. Importantly, the bags or the balloons may be connected to the wrap permanently or during the use. In the second case this may be done by having a small bubble of soft plastic or a series of adhesive-containing bubbles to be placed on the surface of the balloon so that when this unit is pressed the pressure will cause the adhesives to leak out and stick the two sides together. This can also be made by having a layer of adhesive covered by a layer of plastic that has weak points so that squeezing it would cause leakage of the adhesive to occur from the weak spots to the area between the balloon and the wrap. The applicant believes that this is a very valuable technique and may be used in many units and has many uses as well. He also wishes to apply for a patent for this unit in the future.

I claim:

1. A device for wound therapy and prevention of bleeding comprising:

a transparent pressurized balloon adapted to be placed over a body skin wound wherein intact skin is immediately contiguous such a wound;

said pressurized balloon having a lower face adapted to face such a wound and immediately contiguous intact skin;

means disposed beneath said lower face of said balloon comprising an adhesive layer adapted to span such a wound and stick to such immediately contiguous intact skin; and means for holding said balloon in place over such a wound and immediately contiguous intact skin while said adhesive layer sticks to such immediately contiguous intact skin and said balloon applies pressure against such a wound and immediately contiguous skin without obstructing a view through said balloon, wherein said means disposed beneath said lower face of said balloon comprising an adhesive layer adapted to span such a wound and stick to such immediately contiguous intact skin comprises:

an absorbent layer disposed between said adhesive layer and said lower face of said balloon.

2. A device as set forth in claim 1 wherein said adhesive layer comprises:

openings that allow wound secretions to pass through to said absorbent layer.

3. A device as set forth in claim 1 further including:

means for setting a desired amount of inflation of said balloon.

4. A device as set forth in claim 1 wherein said means for holding said balloon in place over such a wound and immediately contiguous intact skin while said adhesive layer sticks to such immediately contiguous intact skin and said balloon applies pressure against such a wound and immediately contiguous skin without obstructing a view through said balloon comprises:

a pliable transparent strip beneath a central portion of which said balloon is disposed such that said strip has an expanse extending in opposite directions beyond said balloon to comprise regions that do not directly overlie said balloon;

said regions comprise lower faces having adhesive layers disposed thereon adapted to stick to skin;

and strippable covering material covering said adhesive layers of said regions and said adhesive layer that spans such a wound.

5. A device as set forth in claim 1 wherein said means disposed beneath said lower face of said balloon comprising an adhesive layer adapted to span such a wound and stick to such immediately contiguous intact skin comprises:

a relatively more rigid than said balloon layer disposed beneath said balloon having a lower face on which said adhesive layer is disposed.

6. A device as set forth in claim 1 wherein said means disposed beneath said lower face of said balloon comprising an adhesive layer adapted to span such a wound and stick to such immediately contiguous intact skin comprises:

a relatively more rigid than said balloon layer disposed beneath said balloon and having a lower face on which an absorbent layer is disposed, and said absorbent layer comprises a lower face on which said adhesive layer is disposed.

7. A device as set forth in claim 1 wherein said means for holding said balloon in place over such a wound and immediately contiguous intact skin while said adhesive layer sticks to such immediately contiguous intact skin and said balloon applies pressure against such a wound and immediately contiguous skin without obstructing a view through said balloon comprises:

material that has an expanse adapted to peripherally bound such intact skin including a lower face adapted to face further intact skin that is beyond, and peripherally surrounds, such immediately contiguous skin;

and an adhesive layer disposed on said lower face of said material peripherally bounding said lower face of said balloon so that when the device is in use, the sticking of said material to such further intact skin by means of said adhesive layer disposed on said lower face of said material prevents blood and wound secretion from oozing out.

8. A device as set forth in claim 7 wherein said means disposed beneath said lower face of said balloon comprising an adhesive layer adapted to span such a wound and stick to such immediately contiguous intact skin comprises:

an absorbent layer and electrode means disposed between said adhesive layer and said lower face of said balloon, and leads extending from said electrode means to provide a signal for indicating fluid absorption by said absorbent layer.

9. A device as set forth in claim 1 wherein said means for holding said balloon in place over such a wound and immediately contiguous intact skin while said adhesive layer sticks to such immediately contiguous intact skin and said balloon applies pressure against such a wound and immediately contiguous skin without obstructing a view through said balloon comprises:

a transparent member disposed in overlying relation to said balloon;

and an adjustable strap system extending from said transparent member adapted to be strapped to a living body to force said transparent member against said balloon.

10. A device as set forth in claim 9 wherein said transparent member and said balloon are shaped to be adapted to fit over a person's groin;

and said adjustable strap system comprises an abdomen strap adapted to extend around a person's abdomen and a thigh strap adapted to extend around a person's thigh.

11. A device for wound therapy and prevention of bleeding comprising:

a transparent pressurized balloon adapted to be placed over a body skin wound wherein intact skin is immediately contiguous such a wound;

said pressurized transparent balloon having a lower face adapted to face such a wound and immediately contiguous intact skin;

means disposed beneath said lower face of said balloon comprising a transparent rigid plastic piece adapted to span such a wound and such immediately intact skin; and means for holding said balloon in place over such a wound and immediately contiguous intact skin while said balloon applies pressure against such a wound and immediately contiguous skin by forcing said transparent, rigid plastic piece toward such a wound and immediately contiguous intact skin while providing a view through said balloon and said piece.

12. A device as set forth in claim 11 wherein said means disposed beneath said lower face of said balloon comprising a transparent, rigid plastic piece adapted to span such a wound and such immediately contiguous intact skin further comprises:

an absorbent layer disposed beneath said rigid plastic piece adapted to overlie such a wound and such immediately contiguous intact skin.

13. A device as set forth in claim 12 wherein said means disposed beneath said lower face of said balloon further comprises an adhesive layer disposed beneath said absorbent layer.

14. A device as set forth in claim 13 including strippable covering material that covers said adhesive layer.

15. A device as set forth in claim 14 wherein said adhesive layer comprises:

openings that allow wound secretions to pass through to said absorbent layer.

16. A device as set forth in claim 11 wherein said means for holding said balloon in place over such a wound and immediately contiguous intact skin while said balloon applies pressure against such a wound and immediately contiguous skin by forcing said transparent, rigid plastic piece toward such a wound and immediately contiguous intact skin while providing a view through said balloon and said piece comprises:

a transparent member disposed in overlying relation to said balloon;

and an adjustable strap system extending from said transparent member adapted to be strapped to a living body to force said transparent member against said balloon;

wherein said transparent member and said balloon are shaped to be adapted to fit over a person's groin;

and said adjustable strap system comprises an abdomen strap adapted to extend around a person's abdomen and a thigh strap adapted to extend around a person's thigh.

* * * * *